(12) United States Patent
Weng et al.

(10) Patent No.: US 8,722,429 B2
(45) Date of Patent: May 13, 2014

(54) PARTICLES

(75) Inventors: Ellen Weng, Oppegård (NO); Geir Fonnum, Fjellhamar (NO); Grete Irene Modahl, Arnes (NO); Astrid Evenrød Molteberg, Fetsund (NO); Erling Sigurd Finne, Hvalstad (NO); Torkel Stene, Oslo (NO)

(73) Assignee: Life Technologies AS, Oslo (NO)

( * ) Notice: Subject to any disclaimer, the term of this patent is extended or adjusted under 35 U.S.C. 154(b) by 358 days.

(21) Appl. No.: 12/486,590

(22) Filed: Jun. 17, 2009

(65) Prior Publication Data

US 2010/0087327 A1   Apr. 8, 2010

Related U.S. Application Data

(63) Continuation of application No. 10/536,230, filed as application No. PCT/GB03/05390 on Dec. 11, 2003, now abandoned.

(30) Foreign Application Priority Data

Dec. 11, 2002  (GB) .................................. 0228914.8

(51) Int. Cl.
*G01N 33/553*   (2006.01)
(52) U.S. Cl.
USPC .......................................... 436/526; 436/525
(58) Field of Classification Search
None
See application file for complete search history.

(56) References Cited

U.S. PATENT DOCUMENTS

| | | | |
|---|---|---|---|
| 4,654,267 A | 3/1987 | Ugelstad et al. | |
| 4,873,102 A | 10/1989 | Chang et al. | |
| 5,089,416 A | 2/1992 | Schwartz et al. | |
| 5,091,206 A | 2/1992 | Wang et al. | |
| 5,283,079 A | 2/1994 | Wang et al. | |
| 5,395,688 A | 3/1995 | Wang et al. | |
| 5,543,054 A * | 8/1996 | Charkoudian et al. | 210/638 |
| 5,597,531 A | 1/1997 | Liberti et al. | |
| 5,736,349 A | 4/1998 | Sasaki et al. | |
| 6,013,531 A | 1/2000 | Wang et al. | |
| 6,133,047 A | 10/2000 | Elaissari et al. | |
| 6,204,033 B1 * | 3/2001 | Muller-Schulte | 435/181 |
| 6,280,618 B2 * | 8/2001 | Watkins et al. | 210/222 |
| 6,456,699 B1 | 9/2002 | Burg et al. | |
| 7,101,680 B2 | 9/2006 | Jackowski et al. | |
| 2002/0057783 A1 | 5/2002 | Kredo et al. | |
| 2002/0160425 A1 | 10/2002 | Jackowski et al. | |
| 2006/0008924 A1 * | 1/2006 | Anker et al. | 436/526 |
| 2006/0131542 A1 | 6/2006 | Weng et al. | |
| 2013/0099151 A1 | 4/2013 | Weng et al. | |

FOREIGN PATENT DOCUMENTS

| | | |
|---|---|---|
| CN | 1174510 | 2/1998 |
| DE | 3836475 | 5/1989 |
| EP | 2051075 | 8/2001 |
| EP | 1175074 | 1/2002 |
| EP | 1178658 | 2/2002 |
| EP | 1573325 | 1/2009 |
| GB | 2307619 | 5/1997 |
| IN | 221649 | 6/2008 |
| JP | 61-132869 | 6/1986 |
| JP | 09-28397 | 2/1997 |
| JP | 59-500691 | 12/2000 |
| JP | 2000-516345 | 12/2000 |
| WO | WO91/09141 | 6/1991 |
| WO | WO99/19000 | 4/1999 |
| WO | WO99/26067 | 5/1999 |
| WO | WO00/61647 | 10/2000 |
| WO | WO01/47218 | 6/2001 |
| WO | WO01/52477 | 7/2001 |
| WO | WO01/69427 | 9/2001 |
| WO | WO2004/053490 | 6/2004 |

OTHER PUBLICATIONS

EP Application No. 091514026, Extended Search Report mailed Mar. 19, 2009.
Ramos et al., "Production of Magnetic Nanoparticles in a Polyvinylpyridine Matrix," Polymer, vol. 41, No. 24, Nov. 2000, 8461-8464.

* cited by examiner

*Primary Examiner* — Shafiqul Haq

(57) ABSTRACT

A coated magnetic particle comprising an optionally porous magnetic polymer particle of a matrix polymer, said polymer particle having on a surface and/or in the pores thereof superparamagnetic crystals, said coated particle having a coat formed of a coating polymer, wherein said coated magnetic particle is essentially non-autofluorescent.

19 Claims, No Drawings

PARTICLES

The present application is a continuation of U.S. application Ser. No. 10/536,230, filed Oct. 20, 2005 (abandoned), which is the national stage filing of International Application No. PCT/GB2003/005390, filed Dec. 11, 2003, which claims priority to United Kingdom Patent Application No. GB0228914.8, filed Dec. 11, 2002, all of which are incorporated herein by reference.

This invention relates to magnetic polymer particles, to processes for their preparation and to their uses. In particular, the invention relates to coated magnetic polymer particles which exhibit low autofluorescence.

Magnetic polymer particles are of general utility in various medical and biochemical fields, for example as transport vehicles for the delivery of pharmaceutical products, for diagnostic purposes, for separation and for synthetic purposes. Such particles rely upon their magnetic properties in order to perform these functions: in diagnostic assay applications, for example, application of a magnetic field to a sample containing an analyte bound to magnetic polymer particles allows the isolation of the analyte without the use of centrifugation or filtration; and in therapeutic applications, for example, application of a magnetic field to the patient may serve to target drug-carrying magnetic polymer particles to a desired body site.

By magnetic is meant herein that the polymer particles contain superparamagnetic crystals. Thus the magnetic polymer particles' are magnetically displaceable but are not permanently magnetizable.

Many processes for preparing magnetic polymer particles are known, a large number of which involve preparing maghemite- or magnetite-containing polymer particles from pre-formed magnetic iron oxides, e.g. magnetite. Some of processes involved are described in U.S. Pat. No. 4,654,267 (Ugelstad) the contents of which are incorporated herein by reference.

Thus U.S. Pat. No. 4,654,267 outlines a number of limitations with regard to the processes which preceded it; these include difficulty in obtaining magnetic particles of similar size and/or of homogeneous or uniform magnetic properties, as well as a more general problem relating to the difficulty of incorporating magnetic material inside the cavities of porous polymer particles.

With deposition taking place principally on the surface, or in large open cavities, leaching of magnetic particles, which shortens the useful lifetime of magnetic polymer particles in the applications to which they are put, was consequently problematic.

In order to overcome these disadvantages, to produce porous magnetic polymer particles having magnetic material disposed within the polymer pores, U.S. Pat. No. 4,654,267 advocated the use of porous polymer particles having surface functional groups which serve to draw the iron ions into the polymer particles. These functional groups could either result from the use of functionalized comonomers in the production of the polymer or from post-polymerization treatment of the polymer to introduce the functional groups, e.g. by coupling to or transformation of existing groups on the polymer surface.

The leaching of superparamagnetic crystals from the porous polymer particles may be further inhibited by forming a further polymer coating over the superparamagnetic crystal loaded polymer particles, or more particularly by at least partly filling the pores of the particles with a polymer coating. Such coating polymers may typically be formed from monomers reactive with functional groups pendant from the surface of the polymer of the underlying particles.

However, when coated magnetic polymer particles are prepared in this way they exhibit the characteristic known as autofluorescence, i.e. they exhibit intrinsic fluorescence. While for many of the uses of coated magnetic polymer particles, e.g. where they are used in syntheses or separations, autofluorescence does not cause problems, where the particles are to be used in assays in which light emissions are detected, autofluorescence by the particles can produce unwanted background signals. The autofluorsecence may also mask the signal from an emitter of interest. This will decrease the sensitivity of the assay.

We have now surprisingly found that the autofluorescence exhibited by a magnetic polymer particle can be minimised by the avoidance of conjugated delocalised electron systems (other than those found in benzene rings) in the matrix polymer, in the particle coating and in any surface functionalities. Such conjugated delocalised electron systems had previously been considered essential to allow attraction of iron oxides in the magnetisation step and polymer coating to occur successfully.

As a result, a matrix polymer with reduced or no tendency to autofluorescence can be used in the preparation of coated magnetic polymer particles which therefore exhibit remarkably low autofluorescence. Such particles may have utility in a variety of assays, in particular assays in which fluorescence is detected.

Whilst the use of fluorescent entities as labels in non-magnetic polymer beads is known, the use of such fluorescent labels in magnetic beads has the advantage of enabling the combination of magnetic sample preparation and detection, i.e. combining instrumentation for automated sample preparation and/or concentration with detection platforms such as flow cytometers, fluorescence microscopes, high resolution array scanners or laser scanning cytometers. These detection devices can all be included in microfluidic devices where the possibility of using the magnetic properties for sample preparation and/or concentration will be important.

Thus viewed from one aspect the invention provides an optionally porous magnetic polymer particle comprising a matrix polymer, with disposed on the surface and/or in the pores thereof superparamagnetic crystals, said matrix polymer preferably being essentially free of conjugated delocalized electron systems and optionally being surface functionalised with groups selected from sulphonic acid, carboxylic acid, amine, and epoxy groups, said particle being essentially non-autofluorescent, e.g. having a level of autofluorescence corresponding to a difference in the Mean Grey Value ($\Delta$MGV) at an excitation wavelength of $450\pm25$ nm for an exposure time of 500 ms or 600 ms of less than 600.

Viewed from another aspect the invention provides a coated magnetic particle comprising an optionally porous magnetic polymer particle of a matrix polymer, said polymer particle having on a surface and/or in the pores thereof superparamagnetic crystals, said coated particle having a coat formed of a coating polymer, wherein said coated magnetic particle is essentially non-autofluorescent, e.g. has a level of autofluorescence corresponding to a difference in the Mean Grey Value ($\Delta$MGV) at an excitation wavelength of $450\pm25$ nm for an exposure time of 500 ms or 600 ms of less than 600 and said coated particle is preferably essentially free of conjugated delocalized electron systems.

By matrix polymer (or polymers) is meant the polymer (or polymers) and, if required, cross-linking agents employed to form the uncoated polymer particle, as further defined in detail below.

By essentially free of conjugated delocalized electron systems is meant that the matrix polymer and if present said coating polymer (i.e. the coated particle itself) do not contain any electronic systems in which delocalisation occurs (other than within a benzene ring).

The uncoated magnetic polymer particles produced by forming superparamagnetic crystals in the pores of porous matrix polymers, optionally surface functionalized e.g. with sulphonic acid, carboxylic acid, amine, or epoxy groups (but not with nitro groups), should be effectively non-autofluorescent. Such uncoated particles (and hence the coated particles) preferably have $\Delta$MGV values of less than 300, especially less than 200, particularly less than 100. Such uncoated particles may be used as intermediates in the preparation of the coated particles of the invention or in end uses where leaching of the superparamagnetic crystals is not problematic.

The $\Delta$MGV for the uncoated and coated particles is more preferably less than 400, particularly below 350, more particularly below 300.

The $\Delta$MGV for the particles is determined using a fluorescence microscope by illumination of a substrate (e.g. glass) surface carrying the particles with light from a 100 W mercury or 75 W xenon lamp filtered through a 450±25 nm excitation band pass filter, with a beam splitter at 480 nm and with the emitted light being filtered through a 520 nm long pass filter. $\Delta$MGV is the difference in the Mean Grey Value determined for a minimum of 30 particles and the Mean Grey Value determined for a similar minimum of background positions (i.e. positions on the substrate) e.g. 25 positions.

Conveniently $\Delta$MGV can be determined using a BX-61 fluorescence microscope from Olympus equipped with a 100 W mercury or 75 W xenon lamp and excitation and emission filters from Chroma Technology and an Uplan-Apo 20× objective. Emission detection can be effected using an F-view digital monochrome CCD camera (4096 grey levels) for an exposure time of 500 ms (Xenon lamp) or 600 ms (mercury lamp) and image analysis to determine the MGV values may be performed using the Analysis software of Soft Imaging Systems.

For autofluorescence determination the particles are either dispersed between parallel glass substrates (e.g. microscope slides) in a liquid medium, e.g. 1:1 by volume mixture of glycerol and 1.5 g/l sodium dodecyl sulphate in water (as in Example 12) or buffered in pH 7.4 phosphate buffer saline (Example 18). Autofluorescence measurement is explained in detail in examples 12 and 18.

The superparamagnetic crystals in the polymer particles used in the particles of the invention may be of any material capable of being deposited in superparamagnetic crystalline form on the surface of a polymer particle or more preferably in the pores of a porous polymer particle. Thus the superparamagnetic crystals in the particles of the invention may be of any element, alloy or compound capable of exhibiting superparamagnetism. Magnetic iron oxides, e.g. magnetite or maghemite are preferred; however the crystals may be of mixed metal oxides or other magnetic material if desired. The total quantity of crystalline magnetic material present is generally more than 1%, preferably more than 3%, desirably more than or equal to 5% (by weight, e.g. up to 40% wt. The percentage is calculated on a Fe (or equivalent metal in the case of magnetic materials other than iron oxides) weight basis based upon the overall dry weight of the coated particles. The superparamagnetic crystals will be on a surface of the matrix polymer, i.e. on the external surface of the particle or, more preferably, on a surface of a pore in a porous matrix particle.

The optionally porous magnetic polymer particle may be prepared by conventional means using monomers. In general any porous non-autofluorescent polymer particles can be used. However, the monomers used in forming the matrix polymer (and the coating polymer) should preferably be such that the resultant polymer is substantially free from conjugated delocalized electron systems other than benzene rings. Thus for example the use of divinylbenzene as a cross-linking agent should preferably be avoided.

Also the presence of nitro groups on the surface of the polymer particle should be avoided since such groups inherently contain delocalised electron systems and therefore contribute to the autofluorescence of the polymer particle.

The matrix polymer is especially preferably vinylic, a styrenic or, especially, an acrylic polymer. Preferred monomers for matrix polymer preparation include methyl methacrylate, methacrylic acid, hydroxyethyl methacrylate, glycidyl methacrylate, butylmethacrylate, acrylic acid, ethyleneglycol dimethacrylate, trimethylolpropane trimethacrylate, trimethylol triacrylate, pentaerythritol tetraacrylate and other acrylic or methacrylic monomers.

The matrix polymer is preferably not water-swellable.

In one preferred embodiment of the invention, the matrix polymer may be produced by a seeded polymerization reaction, i.e. a multistage polymerization in which the particulate polymer from one stage is used as a seed for a subsequent polymerization reaction in which a larger dimension particulate is produced. In this embodiment, the monomers used in one stage need not be the same as those used in the other stage(s). In this embodiment, the polymer produced in the final stage is preferably an acrylic polymer. The polymer produced in the initial polymerization stage is preferably a styrenic polymer. In an especially preferred embodiment the initial polymer (the seed) is styrenic, an intermediate polymer is a styrenic/acrylic copolymer, and the final polymer is acrylic.

The matrix polymer containing particles may be prepared by any technique suitable for producing particulate polymer particles, e.g. suspension polymerization, emulsion polymerization, dispersion polymerisation etc. However, the particles are especially preferably produced using the well known Ugelstad process, e.g. as described in U.S. Pat. No. 4,654,267 or WO00/61647. Preferably however, ammonia is employed in the magnetisation process instead of ethylene diamine. The use of ammonia has been surprisingly found to give rise to particles having lower levels of autofluorescence.

Thus, prior to incorporation of the magnetic particles it is possible to introduce amino groups onto the particle surface using ammonia.

Particles may be produced using the Ugelstad process which are substantially monodisperse, i.e. the coefficient of variation (CV) of the particle diameter is very small, e.g. 2 to 5%. CV is defined as 100 times (standard deviation) divided by mean where mean is mean particle diameter and standard deviation is standard deviation in particle size. CV is preferably calculated on the main mode, ie. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyzer.

The coating polymer is preferably formed from at least one epoxide compound, preferably at least two epoxide compounds.

The reaction of the porous magnetic polymer particle with the coating monomers generates a coating polymer within the pores of the matrix polymer particles which serves essentially to block these pores, physically encapsulating the superparamagnetic crystals within the polymer particles. The resulting "coated" particles then have reduced porosity relative to the porous starting material. Surprisingly it is believed that the superparamagnetic crystals appear to catalyse the polymerization so that the coating forms preferentially in their vicinity. Since the majority of the superparamagnetic crystals are within pores in the starting porous particles, the coating may not form to any significant extent on the external surface of the particles.

In one preferred embodiment, the porous polymer particles are reacted with a mixture of epoxides. Preferably, the epoxides contain at least one ether link and optionally a hydrophobic component, e.g. a alkylene chain. Generally the epoxides will have a carbon atom content of from 3 to 50, preferably 3 to 25. Typical epoxides that may be used include epichlorohydrin, epibromohydrin, isopropylglycidyl ether, butyl glycidyl ether, allylglycidyl ether, 1,4-butanediol diglycidyl ether (1,4-bis (2,3-epoxypropoxy)butane), neopentylglycol diglycidyl ether, ethylene glycol diglycidyl ether, glycerol diglycidyl ether, glycidol, and glycidyl methacrylate, ethyl hexyl glycidylether, methyl glycidylether, glycerol propoxylate triglycidylether, poly(propylene glycol)diclycidylether, 1,3 butanediol diglycidylether, tert-butyl glycidylether, 1,4 cyclohexanedimethanol diglycidyl ether, diethylene glycol diglycidyl ether, dodecyl glycidylether, O-(2,3 epoxypropyl)-O'-methylpolyethylene glycol glydidylether, glycidyl tetrafluoroethyl ether, 1,6 hexanediol diglycidylether, octyl glycidylether, decyl glycidylether, poly (epichlorohydrin-co-ethylene oxide-co-allyl glycidylether), polyethylene glycol diglycidyl ether, trimethylolethane triglycidylether, trimethylolpropan, triglycidylether, tert-butyldimehytlsilyl glycidylether, 1,2-epoxybutane, 1,2-epoxypentane, 1,2-epoxy-5-hexene, 1,2-epoxy-hexane, 1,2-epoxy-7-octene, 1,2-epoxyoctane, 1,2,7,8-Diepoxyoctane, 1,2-Epoxy-9-decene, 1,2-Epoxydecane, 1,2-Epoxydodecane, 1,2-Epoxytetradecane etc.

Typically, the coating reaction may be effected by impregnating the porous magnetic polymer particle with the coating monomers e.g. using a solution of these (for example in an organic solvent such as methanol, toluene, xylene, diethylenglycol, dimethyl ether or diglyme) or by mixing a dispersion of the porous particles in an organic solvent with a liquid epoxide mixture. Sonication may be used to improve impregnation and the reaction may be accelerated by raising the temperature, e.g. to 50-100° C. Any solvent used may be extracted by application of sub-ambient pressure.

Viewed from a further aspect the invention provides a process for the preparation of coated magnetic particles as herein before described being free of conjugated delocalised electron systems, said method comprising reacting porous magnetic polymer particles essentially free from surface nitro groups and having superparamagnetic crystals on the surface and/or in the pores thereof with polymer-forming monomers selected from epoxides.

Viewed from a further aspect the invention provides the use of such particles in syntheses, extractions or assays.

If desired further materials may be impregnated into or chemically attached to the particles either before the coating polymerization reaction or after coating polymerization. Typically such further materials will be radiation emitters or absorbers, e.g. fluorophores, material giving luminescence, material giving time delayed fluorescence, chromophores or radioactively labelled materials.

Particles according to the present invention will generally have sizes (i.e. diameters) that are generally in the micrometer range, e.g. 0.3 to 100 µm, especially 0.5 to 50 µm, more especially 0.8 to 10 µm, e.g. 2 to 10 µm, e.g. 5 and 8 µm.

Typically the porous particles used will have a surface area of at least 15 m$^2$/g (measured by the BET nitrogen absorption method), and more preferably at least 30 m$^2$/g, e.g. up to 700 m$^2$/g, when corrected to a mean particle diameter of 2.7 µm (i.e. multiply surface area by 2.7/MD, where MD is the mean diameter in micrometers). Similarly scaled, the particle pore volume is preferably at least 0.1 mL/g.

Typically, the polymer particles are spherical and substantially monodisperse before they are coated and especially preferably remain spherical and substantially monodisperse once they have been coated.

By substantially monodisperse it is meant that for a plurality of particles (e.g. at least 100, more preferably at least 1000) the particles have a coefficient of variation (CV) of less than 20%, for example less than 15%, preferably less than 12%, more preferably less than 11%, still more preferably less than 10% and most preferably no more than about 8%, e.g. 2 to 5%.

Generally, the uses to which magnetic polymer particles are put, e.g. their use as diagnostic tools, require an appropriate degree of electrophilicity in order that they may participate adequately in coupling and other reactions in aqueous systems prevalent in biological media.

Whilst the general polarity of the coatings is desirably electrophilic, certain coatings which contain hydrophobic moieties may be incorporated so as to tailor the degree of electrophilicity to that which is desired. In this way, the invention permits the provision of useful diagnostic and other tools having a wide range of polarities.

If desired the surfaces of the coated magnetic polymer particles may be further functionalised, e.g. by coupling a drug molecule, a reporter label (e.g. a chromophore, enzyme or radiolabel), or an affinity ligand (e.g. an antibody or antibody fragment, a member of a specific binding partner pair (e.g. biotin or streptavidin), an oligopeptide, an oligonucleotide, or an oligosaccharide).

Such coupling may be direct or indirect (and so may or may not involve the use of a coupling agent to form a linkage between the particle and the substance being coupled to it) and may be biodegradable or non-biodegradable. Biodegradable couplings may be desired if the magnetic polymer particles are to be used for the targeted release of an active compound. Accordingly after coating has been effected, the pendant groups of the coating may be manipulated to provide appropriate functionality (for example epoxy, hydroxy, amino, ketones, mercapto, isothiocyanate, isocyanate, tosyl, carboxylic acid etc functionalities) for the attachment of such substances.

The low autofluorescence particles of the invention are of particular use in applications where the fluorescence of the particle is to be detected, e.g. in an assay where a reporter carries a fluorophore. By fluorophore is meant a compound which exhibits intrinsic fluorescence. In some assays it may be preferable to employ coloured particles or beads. In this regard, coloured particles/beads for use in such assays require the presence of a fluorophore to "colour code" the particle. Many different fluorophores are known allowing the preparation of a variety of colour coded beads, (i.e. each bead class emitting light at distinct wavelengths, different intensity etc when excited by light of a lower wavelength. The excitation source can be laser(s) or filtered light of one or several wavelengths). Such coding may be constructed by, for example, providing beads of differing fluorescence intensity, with differing fluorescence spectra, differing intensity-ratio between two or more fluorophores, or by using beads of differing diameters with various fluorophores. Other possible coding methods may be use of magnetic tags, refractive index, adsorption spectrums, adsorption ratios etc.

Fluorophores can be attached to the low autofluorescence particles of the invention by, for example, contacting a particle having surface functional groups, e.g. amino groups, with a fluorophore comprising a reactive group forming covalent attachment of the fluorophore to the particles. Such functional groups may be succinimidyl esters, isothiocyanates, carboxylic acids, maleimides, sulphonyl chlorides etc.

Other potential methods for incorporation of fluorophores onto (or into) the beads may involve hydrophobic or electrostatic interactions, swelling of the fluorophores into the coating and entrapment (or capture) of the fluorophores in the coating (entrapment may be induced by change of polarity of the solvents used), deposition of fluorophores in pores, swelling fluorophores into polymer matrix etc.

The attachment of the fluorophore to the particle can be achieved at any suitable stage of the particle synthesis. Thus, a fluorophore may be attached to the particle after the magnetisation process but before a coat is subsequently applied. Alternatively, a thin coat may be applied to the particle prior to the fluorophore being added and a subsequent further coat applied. Most conveniently however, the fluorophore is attached to the particle after the final coat has been applied.

The latter process is most favoured since the application of a coat over the fluorophore may significantly reduce its fluorescent intensity although for the coumarin dye AMCA (from Molecular Probes Inc.) intensity reduction is not observed if a coating is placed over it.

The reaction between the particle and the fluorophore should conveniently take place in an organic solvent such as dimethylformamide, acetonitrile, acetone, 1,4-dioxane, chloroform, methanol, ethanol, toluene, butylacetate, ethylacetate etc alone or mixtures thereof; what is primarily required is a solvent system which allows a homogenous distribution of dye to all the particles and allows incorporation of dye in high yield. This will be readily carried out by the person skilled in the art.

The fluorophore functionalised coated magnetic particle should also carry an affinity ligand, the nature of which will be selected based on its affinity for a particular analyte whose presence or absence in a sample is to be ascertained. The affinity ligand may therefore comprise any molecule capable of being linked to a magnetic probe which is also capable of specific recognition of a particular analyte. Affinity ligands therefore include monoclonal antibodies, polyclonal antibodies, antibody fragments, nucleic acids, oligonucleotides, proteins, oligopeptides, polysaccharides, sugars, peptides, peptide encoding nucleic acid molecules, antigens, drugs and other ligands. Most commonly the affinity ligand is an antibody which binds to an antigen in a sample. Examples of suitable affinity ligands are available in the published literature and are well known. The use of further binding partners, secondary affinity ligands and linking groups is routine in the art and it will be appreciated that the use of such species with the particles of the invention is possible if desired.

More specifically, nucleic acid detection generally involves probing a sample thought to contain target nucleic acids using a nucleic acid probe that contains a nucleic acid sequence that specifically recognises, e.g. hybridises with, the sequence of the target nucleic acids, such that the nucleic acid affinity ligand and the target nucleic acids in combination create a hybridisation layer. Correspondingly, immunoassay type detection of hormones, antibodies, cytokines etc generally involves binding of an antibody or an antigen to the beads. It may also be of interest to bind ligands that have specific affinity for "tags" which have been introduced on the target of interest. Such ligands can be a metal chelate, small organic molecule, nucleic acid derivative or protein. For applications in cellular biology and microbiology it will be of interest to bind antibodies with affinity for special cell types, bacteria or viruses.

The target material is optionally a biological molecule or molecule of synthetic origin, or conjugation of the two types, e.g. it may be a molecule or a group of molecules, cells or a single cell organism or a virus including for example antibodies, amino acids, proteins, peptides, polypeptides, enzymes, enzyme substrates, hormones, lymphokines, metabolites, antigens, haptens, cytokines, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatised nucleic acids, DNA, RNA, natural or synthetic drugs, receptors, virus particles, bacterial particles virus components, cells, cellular components, natural or synthetic lipid vesicles, polymer membranes, polymer services and particles and glass and plastic surfaces.

As well as being coupled to such target-binding ligands, the particles produced according to the invention may also be subsequently labelled with a reporter moiety, e.g. biotin, a chromophore, fluorophore, radioisotope or enzyme.

Of particular further interest is the possibility of including a fluorophore as a reporter moiety especially in conjunction with a colour coded particle as described above. The incorporation of a fluorophore into a reporter molecule is known in the art.

For example, in nucleic acid detection, an oligonucleotide probe complementary to the target, labelled with one or several fluorophores can be employed. Labelling may be achieved by e.g. using modified phosphoramidites during probe synthesis.

Alternatively, enzymatic incorporation of labelled nucleotdies or probes can be employed when the target is present.

For protein/immunoassays, an antibody or antigen can be labelled using standard cross-linking reagents; e.g. N-hydroxybuccinimide activated fluorophores which react with amino groups on the protein or antigen.

When such a reporter is combined with a low autofluorescence particle of the invention already attached to a "colour coding" fluorophore the presence of two excitable fluorophores exists. This allows the beads to be utilised in a variety of assays as described in more detail below and allows multiplexing.

The fluorophores utilised should be chosen such that their excitation and emission signals do not interfere. Whilst the person skilled in the art can tailor the fluorophores they use to minimise overlap, because many fluorophores have a absorption spectrum which exhibit a tail at wavelengths shorter than the absorption maximum and further to avoid excitation of the code with the excitation light intended for the reporter, preferably the code (i.e. particle fluorophore) should be set at shorter wavelengths than the reporter. Moreover, the shorter wavelength region (blue and green emission) is also the region of the spectrum where inherent autofluorescence is most significant.

In a particularly preferred embodiment of the invention therefore, the fluorophore attached to the particle will emit in the blue region of the spectrum (i.e. at shorter wavelengths that the reporter) whereas the fluorophore attached to the reporter moiety will emit in the red region of the spectrum (i.e. at longer wavelengths than the particle fluorophore).

Alternatively viewed, the colour fluorophore (code) attached to the particle will emit at shorter wavelengths than the reporter whereas the fluorophore attached to the reporter moiety will emit at longer wavelengths than the code.

Suitable fluorophores of use are listed below: 7-Hydroxy-4-methylcoumarin (AMCA/AMCA-X), Alexa fluor 350, Alexa fluor 405, Alexa Fluor 430, Alexa Fluor 488, Alexa Fluor 532, Alexa Fluor 546, Alexa Fluor 568, Alexa Fluor 594, Alexa Fluor 633, Alexa Fluor 647, BODIPY 493/503, BODIPY 530/550, BODIPY 558/568, BODIPY 564/570, BODIPY 576/589, BODIPY 581/591, BODIPY 630/650-X, BODIPY 650/665-X, BODIPY FL, BODIPY TMR, BODIPY TR, Cascade Blue, Cy2, Cy3, Cy3.5, Cy5, Cy5.5, Cy7, DY-505, DY-555, DY-647, Oregon Green 488, Oregon Green 500, Oregon Green 514, Pacific Blue, Pyrene, Tetramethylrhodamine, Fluorescein, with or without suitable functional groups and with or without a linker between the fluorophore and the functional group. The fluorophores may have appropriate functional groups e.g. amino, succinimidylester, isothiocyanates, maleimide, sulphonyl chloride, carboxylic acid etc.

Such fluorescently labelled particles can be used in various assays e.g. multiplexed immunoassays. For example, a mixture of particles with different colour codings and corresponding affinity ligands may be added to a sample to be analysed. The analyte of interest will bind by affinity to its corresponding ligand on the coloured magnetic particles.

In a sandwich type immunoassay, a label (e.g. a fluorophore) bound to a second antibody (affinity ligand) specific to the analyte is then bound to the captured analyte. The label may be selected from the group of well-known labels such as radioimmunoassay, fluorescent or chemiluminescence immunoassay, or immunoPCR technology. Extensive discussion of the known immunoassay techniques is not required here since these are known to those of skilled in the art." Jackowski, George; et al., US Patent application 20020160425, Oct. 31, 2002).

The magnetic properties of the particle are used to facilitate simple (automated) washing of the bound complex in order to remove any unbound label and other reagents that will interfere during the detection step. The degree of interference in the absence of a washing step will depend on the nature of the system used but in most cases it is essential to remove any unbound label. In all cases, the result of washing is lowered background and increased signal to noise ratio compared to an analysis without washing.

The particle-analyte-label complex is then subjected to analysis in one or two detection systems where a) the colour of the beads is detected and b) the label bound is detected. This can be done simultaneously in the same detector, in two parallel detectors or successively by using the same detector twice or by moving the bead complex from one detection system to another. In the latter case it must be possible to track particles so that there is a direct link between the particle colour and label detection.

Multiplexing is achieved by the colour coding of the particles. By identifying which particle type has a signal from an associated label, the analyte can be identified. Using two or more different labels for detection of analytes can increase the level of multiplexing.

The detection system must be able to analyse single particles. This can be done in a flow based system such as a microfluidic flow cytometer or in an immobilised bead array format. In the later case, the beads are deposited passively or actively by affinity or magnetic force to a solid surface such as a microscope slide, bottom of microtitre well or structure in a microfluidic system. The colour coding of the beads can be read using a high resolution scanner while detection of labels on the surface of the beads will need more sophisticated equipment such as a microscope based image analysis system.

The detection limit of the system is determined by the detector's ability to identify labels on the surface of the beads. The sensitivity can thus be increased if more labels are introduced per analyte or the label introduced is very large (in the sense easy to detect).

In competitive assays, an added labelled (e.g. with a fluorophore) analyte competing with the analyte of interest is employed. An affinity ligand (antibody) with equal affinity for the natural analyte and the labelled analyte is immobilized on the colour coded beads, so that each set of colour coded beads has specific affinity for one set of analytes.

The assays contemplated can utilise bead array technology. In a bead array format, particles can be (passively) spotted or positioned in confined areas on a surface using magnetism. The results of the bead array are read in a two-step method in which the beads are decoded. The position of each bead and its colour coding is recorded by a suitable software and the signal from positive beads is recorded and correlated with the nature of its coding.

Alternatively, a labelled reporter need not be used and instead the analyte may be further reacted in such a way that it is bound by biotin or a/biotinylated molecule is bound to the bead/analyte complex. This can then be bound to a streptavidin coated slide and analysed by microscopy or laser scanning.

In a microfluidic competitive multiplexed immunoassay the bead may act as both reporter and label. Beads may be coated with an antibody against the target antigen. Multiplexing is achieved by using one colour coding for each antibody-antigen pair of interest. A standard competitive assay may then be carried out in the presence of a biotinylated antigen. This can be achieved in any suitable vessel, e.g. a tube, well, or a microfluidic device.

After incubation, magnetic separation is used to wash the bead-antigen complex free of unincorporated antigens. The samples are then passed over a streptavidin coated surface. Using optimised flow or washing conditions, only the bead complexes with competitive, biotinylated antigens are bound. Thus, samples containing high concentration of a target antigen will have low or no beads with the corresponding colour coding bound, while there will be a high number of beads bound of a colour coding corresponding to a low concentration target.

The microfluidic device can be a simple as a defined area on a microscope slide, and can be made by microarray spotting of streptavidin. Alternatively, more complex solutions can be made incorporating mixing, magnetic separation and detection in the microfluidic device.

Thus, viewed from another aspect the invention provides use of the particles of the invention in an assay which comprises the steps of:
i) adding a coated magnetic particle comprising a first fluorophore and an affinity ligand to a sample in which a target analyte may be present;
ii) allowing said affinity ligand to bind with said analyte if present to form a complex;
iii) contacting the complex with a reporter to allow binding of said reporter to said analyte wherein said reporter optionally carries a second fluorophore;
iv) magnetically separating said particles from said sample; and
v) detecting said first fluorophore and if present said second fluorophore.

or an assay which comprises the steps of:
i) contacting a coated magnetic particle comprising a first fluorophore and an affinity ligand with a sample in which a target analyte may be present and in which an analyte carrying a reporter capable of competing with said target analyte for the affinity ligand is present:
ii) allowing said affinity ligand to bind to said analyte, if present, or said analyte carrying a reporter;
iii) magnetically separating said particles from said sample; and
iv) detecting the first fluorophore.

Whilst assays have been described here with reference to fluorophores, it would of course be possible to use other labels in conjunction with fluorophores. For example, differently sized beads could be employed or beads labelled with radio labels.

The invention will now be described further by reference to the following Examples. These are not intended to be limitative but merely exemplary of the invention.

In the Examples percentages are by weight unless specified otherwise.

EXAMPLE 1

Seed Latex 18.0 g of a polystyrene latex with 0.5 micrometer monosized particles made by emulsion polymerisation was stirred at room temperature together with an emulsion of 10.8 g dioctanoyl peroxide and 10.8 g acetone in 108.6 g 0.6% sodium dodecyl sulphate (SDS) in water. After 20 hours, the reaction mixture was added to an emulsion of 93.3 g methyl methacrylate and 93.3 g styrene in 859.1 g of 0.25% SDS-solution. After stirring for 2 hours at 25 W, 803.4 g of a solution of 0.05% KI in water was charged into the reactor and the temperature was raised to 70° C. for 10 hours. After polymerisation, a seed latex containing 8.6% dry substance of 1.9 micrometer monosized particles was obtained.

EXAMPLE 2

Porous Epoxy Particles 34.5 g of the particles of Example 1 was mixed with an emulsion of 5.9 g dioctanoyl peroxide and 5.9 g acetone in 59.1 g 0.5% SDS in water. After stirring for 24 hours at room temperature, the reaction mixture was added to an emulsion of 51.8 g glycidyl methacrylate, 51.8 g ethylene glycol dimethacrylate and 103.6 g butyl acetate in 1013 g of a 0.1% solution of hydroxypropyl methylcellulose in water. The suspension was stirred for 2 hours at room temperature and 474.5 g of a 0.44% solution of hydroxypropyl methylcellulose in water was added. The temperature was raised slowly to 70° C. and the particles were polymerised for 5 hours. After purification with methanol, monosized particles with diameters of 7.5 micrometers were obtained. By nitrogen adsorption, the specific surface area was determined to be 19.2 m$^2$/g dry substance. Auto-fluorescent of these particles could not be observed by fluorescence microscopy or flow cytometry.

EXAMPLE 3

Superparamagnetic Particles from Epoxy Particles 3.3 g FeCl$_2$×4H$_2$O and 7.9 g FeCl$_3$×6H$_2$O were dissolved in 53 g water and added to a dispersion of 5 g dry substance of the porous epoxy particles of Example 2 in 61 g water. The suspension was cooled to 50C and stirred for a few minutes before 62 ml of 25% NH$_3$ in water was added. The temperature was raised to 80° C. for 2 hours. The suspension was cooled and the particles were purified with water by several cycles of centrifugation. After purification, the particles were transferred to methanol and analysed by fluorescence microscopy. No autofluorescence could be observed under the same conditions as would show considerable autofluorescence for conventional magnetic polymer particles. The iron content was determined to be 67 mg Fe/g Dry substance (DS). The particles showed superparamagnetic behaviour and were attracted to a magnet.

EXAMPLE 4

Coating of Superparamagnetic Particles 3 g dry substance of the magnetic particles of Example 3 were transferred to 15 g diglyme by centrifugation and resuspension. The suspension was stirred and 10 g butanediol diglycidyl ether and 5 g glycidol were added. The temperature was raised to 90° C. for 20 hours. The particles were purified with methanol. FT-IR absorption of 1080 cm$^{-1}$ confirmed appearance of ether coating from the epoxides. The particles were analysed by fluorescence microscopy. No green or red autofluorescence was observed.

The particles of Examples 6, 8 and 11 can be coated analogously.

EXAMPLE 5

Porous Particles with Sulphonic Groups 10 g dry substance of the porous epoxy particles of Example 2, suspended in 100 ml water were mixed with 12.6 g sodium sulphite and 13.55 g sodium tetrabutyl ammonium hydrogen sulphate. The mixture was stirred for 20 hours at 80° C. After purification with water, FT-IR absorption of 1035 cm$^{-1}$ confirmed introduction of sulphonic groups.

EXAMPLE 6

Superparamagnetic Particles from Particles with Sulphonic Groups 3.3 g FeCl$_2$×4H$_2$O and 7.9 g FeCl$_3$×6H$_2$O were dissolved in 53 g water and added to a dispersion of 5 g dry substance of the particles of Example 5 in 96 g water. The suspension was cooled at 5° C. and stirred for a few minutes before 62 ml of 25% NH$_3$ in water was added. The temperature was raised to 80° C. for 2 hours. The suspension was cooled and the particles were purified with water by several cycles of centrifugation. After purification, the particles were transferred to methanol and analysed by fluorescence microscopy. No autofluorescence could be observed under the same conditions as would show considerable autofluorescence for conventional magnetic polymer particles. The beads were attracted to a magnet and showed superparamagnetic behaviour. The content of iron was determined to be 75.5 mg/g DS and the content of sulphur was determined to be 0.28 mmol/g DS.

EXAMPLE 7

Porous Particles with Carboxylic Groups 28.8 g of the seed latex of Example 1 was mixed with an emulsion of 6.4 g dioctanoyl peroxide and 10.6 g acetone in 106.5 g 0.5% SDS in water. After stirring for 24 hours at room temperature, the reaction mixture was added to an emulsion made from 20.7 g methacrylic acid, 83.0 g ethylene glycol dimethacrylate, 103.7 g butyl acetate, 0.23 g SDS and 975 g of a 0.8% solution of polyvinyl pyrrolidone in water. The suspension was stirred for 2 hours at room temperature and 470 g water was added. The temperature was raised slowly to 70° C. and the particles were polymerised for 5 hours. After purification with methanol, monosized particles with diameters of 8.3 micrometers were obtained. By nitrogen adsorption, the specific surface area was measured to be 210 m²/g DS.

EXAMPLE 8

Superparamagnetic Particles from Carboxylic Particles 2.2 g $FeCl_2 \times 4H_2O$ and 3.0 g $FeCl_3 \times 6H_2O$ were dissolved in 106 g water and added to a dispersion of 5 g dry substance of the particles of Example 7 in 44 g water. The suspension was stirred for some minutes before 51 ml of 25% $NH_3$ in water was added. The temperature was raised to 80° C. for 1 hour. The suspension was cooled and the particles were purified with water by several cycles of centrifugation. After purification, the particles were transferred to methanol and analysed by fluorescence microscopy. No autofluorescence could be observed under the same conditions as would show considerable autofluorescence for conventional magnetic polymer particles. The particles were attracted to a magnet and the content of iron was determined to 42 mg/g DS.

EXAMPLE 9

Porous Epoxy Particles 32.0 g of the particles of Example 1 was mixed with an emulsion of 6.8 g dioctanoyl peroxide and 11.3 g acetone in 114.1 g 0.5% SDS in water. After stirring for 24 hours at room temperature, the reaction mixture was added to an emulsion of 57.6 g glycidyl methacrylate, 57.6 g trimethylolpropane trimethacrylate, 115.2 g butyl acetate, 0.26 g SDS and 1085 g of a 1.1% solution of polyvinyl pyrrolidone in water. The suspension was stirred for 2 hours at room temperature and 521 g water was added. The temperature was raised slowly to 70° C. and the particles were polymerised for 5 hours. After purification with methanol, monosized particles with diameters of 7.5 micrometers were obtained. By nitrogen adsorption, the specific surface area was measured to be 64 m2/g DS. Auto-fluorescence of these particles could not be observed by fluorescence microscopy.

EXAMPLE 10

Porous Amino Particles 78 g dry substance of the particles of Example 9, were transferred to methanol and mixed with 1550 ml of 25% $NH_3$ in water. The suspension was stirred at 60° C. overnight, before the particles were purified with water. The content of primary amino groups was determined to be 0.8 mmol/g DS by a ninhydrin reaction method.

EXAMPLE 11

Superparamagnetic Particles from Amino Particles 3.9 g $FeCl_2 \times 4H_2O$ and 7.9 g $FeCl_3 \times 6H_2O$ were dissolved in 100 g water and added to a dispersion of 10 g dry substance of the particles of Example 10 in 60 g water. The suspension was stirred for some minutes before 81 ml of 25% $NH_3$ in water was added. The temperature was raised to 80° C. for 2 hours. The suspension was cooled and the particles were purified with water by several cycles of centrifugation. After purification, the particles were transferred to methanol and analysed by fluorescence microscopy. No autofluorescence could be observed under the same conditions as would show considerable autofluorescence for conventional magnetic polymer particles. The particles were attracted to a magnet and showed superparamagnetic behaviour. The content of iron was determined to be 73 mg/g DS.

EXAMPLE 12

Measurement of Autofluorescence by Fluorescence Microscopy

Instrumentation and Software

The autofluorescence of superparamagnetic particles was measured with a BX-61 fluorescence microscope from Olympus. The microscope was equipped with a 100 W mercury lamp and filter cubes from Chroma Technology. The autofluorescence was measured through a filter cube with an excitation band pass-filter at 450 nm+/−25 nm. a beam splitter at 480 nm, and emission band pass filter at 520 nm. The objective used was an Uplan-Apo 40×. The signal was detected with a F-view digital monochrome CCD camera (4096 grey levels). The exposure times were 600 ms in all the analyses.

The imaging analyses were performed with a software package, Analysis, from Soft Imaging Systems. The mean grey value of a particle population (MGV) is calculated as the mean of the mean intensity for each particle, resulting in an intensity value, that adjust for the differences in particle area. The results are given as Mean Grey Value for the particles. To obtain comparable values for the auto-fluorescence of the different types of particles, the greyness values for the background have to be subtracted. The particle autofluorescence values are therefore calculated as the difference in Mean Grey Values between the particles and the background.

Sample Preparation

The particle samples were diluted with a 1:1 mixture by volume of 1.5 g g/L SDS in water and glycerol.

Two strips of a two-sided tape (3M Scotch 136 D) were attached to a microscope slide, with a distance between the strips of approximately 3 mm. A microscope cover glass was attached on the top of the strips to give a capillary channel between the slide and the cover glass. The diluted particle samples were mounted into the cannels by capillary forces, and the particles were allowed to settle before measurements were performed.

Results

Two different types of uncoated magnetic polymer particles having a styrene/divinylbenzene matrix polymer and the uncoated particles of Examples 3, 6, 8 and 11 were investigated. The results are given in Table 1.

In Table 2 the results are given for coated magnetic polymer particles. Three different types of coated magnetic polymer particles having a styrene/divinylbenzene matrix polymer and the coated particles of Example 4 were investigated.

The autofluorescence of the particles is given as the difference (Δ MGV) between the Mean Grey Value of the particles and the Mean Grey Value of the background.

TABLE 1

| Sample | Description | Particle Auto-fluorescence given as Δ MGV | Raw data from measurement | |
|---|---|---|---|---|
| | | | MGV Particles | MGV Background |
| A | S/DVB | 411 | 1016 | 605 |
| B | S/DVB | 411 | 1053 | 642 |
| C | Ex 3 | 83 | 678 | 595 |

TABLE 1-continued

| | | Particle Auto-fluorescence given as Δ MGV | Raw data from measurement | |
|---|---|---|---|---|
| Sample | Description | | MGV Particles | MGV Background |
| D | Ex 6 | 79 | 686 | 607 |
| E | Ex 8 | 51 | 796 | 745 |
| F | Ex 11 | 62 | 595 | 533 |

TABLE 2

| | | Particle Auto-fluorescence given as Δ MGV | Raw data from measurement | |
|---|---|---|---|---|
| Sample | Description | | MGV Particles | MGV Background |
| G | S/DVB | 769 | 1409 | 640 |
| H | S/DVB | 1423 | 2087 | 664 |
| I | S/DVB | 1277 | 1905 | 628 |
| J | Example 4 | 287 | 971 | 684 |

EXAMPLE 13

Coating of Superparamagnetic Particles 0.5 gram of particles with diameter 5.1 µm, obtained by the method described in example 11, were transferred to 9.5 gram diglyme. 4.6 gram glycidol was added. The suspension was shaken for 20 hours at 75° C. The particles were purified with diglyme and methanol. FT-IR adsorption of 1080 cm$^{-1}$ confirmed appearance of ether coating from the epoxide. The particles were analysed by fluorescence microscopy.

EXAMPLE 14

Coating of Superparamagnetic Particles 0.5 gram of particles with diameter 5.1 µm, obtained by the method described in example 11, were transferred to 9.5 gram toluene. 3.6 gram butandiol diglycidylether and 8.3 ethyl hexyl glycidylether were added. The suspension was shaken for 20 hours at 75° C. The particles were purified with toluene and methanol. FT-IR adsorption of 1080 cm$^{-1}$ confirmed appearance of ether coating from the epoxides. The particles were analysed by fluorescence microscopy.

EXAMPLE 15

Coating of Superparamagnetic Particles 0.5 gram of particles with diameter 5.1 µm, obtained by the method described in example 11, were transferred to 9.5 gram diglyme. 2.3 gram butyl glycidylether and 3.3 gram glycidol were added. The suspension was shaken for 20 hours at 75° C. The particles were purified with diglyme and methanol. FT-IR adsorption of 1080 cm$^{-1}$ confirmed appearance of ether coating from the epoxides. The particles were analysed by fluorescence microscopy.

EXAMPLE 16

Coating of Superparamagnetic Particles 0.5 gram of particles with diameter 5.1 µm, obtained by the method described in example 11, were transferred to 9.5 gram toluene. 3.3 g glycidol and 3.6 g butandiol diglycidylether were added. The suspension was shaken for 20 hours at 75° C. The particles were purified with toluene and methanol. FT-IR adsorption of 1080 cm$^{-1}$ confirmed appearance of ether coating from the epoxides. The particles were analysed by fluorescence microscopy.

EXAMPLE 17

Amino Particles 15 gram particles, obtained by the methods described in example 16, was added to a mixture of 135 gram diglyme and 135 gram ethylenedioxy diethylamine. The dispersion was heated to 60° C. After 4 hours the particles were purified with methanol and anhydrous dimethylformamide. Primary amino groups in the particles were verified by a ninhydrin reaction method. The particles were analysed by fluorescence microscopy and flowcytometry.

EXAMPLE 18

Measurement of Autofluorescence by Fluorescence Microscopy

Instrumentation and Software

The autofluorescence of superparamagnetic particles from Examples 13-17 was measured with a BX-61 fluorescence microscope from Olympus. The microscope was equipped with a 75 W xenon lamp and filter cubes from Chroma Technology. The autofluorescence was measured through three different filter cubes using the exposure times as shown in table 3. The objective used was an Uplan-Apo 20×. The signal was detected with an F-view digital monochrome CCD camera (4096 grey levels). The imaging analyses were performed with a software package, Analysis, from Soft Imaging Systems. The mean grey value of a particle population (MGV) is calculated as the mean of the mean intensity for each particle resulting in an intensity value, which adjusts for the differences in particle area. The results are given as Mean Grey Value for the particles. To obtain comparable values for the autofluorescence of the different types of particles, the greyness values for the background have to be subtracted. The particle autofluorescence values are therefore calculated as the difference in Mean Grey Values between the particles and the background.

TABLE 3

| | | Filter Settings | | |
|---|---|---|---|---|
| Exposure Time | Filter Cube | Excitation | Beam Splitter | Emission |
| 500 ms | 1 | 450 (50) nm | 480 nm | 520 nm long pass |
| 5000 ms | 2 | 550 (30) nm | 580 nm | 620 (60) nm |
| 50000 ms | 3 | 630 (30) nm | 650 nm | 665 nm long pass |

Sample Preparation

All the particles were diluted with phosphate buffer saline (pH 7.4) before transferring to a capillary channel of the microscope slide, as described in example 12.

Results

Two different types of coated magnetic polymer particles having a styrene/divinylbenzene matrix polymer and the coated particles of Examples 13, 14, 15, 16 and 17 were investigated. The results given in Table 4 are also compared to commercial available calibration particles, Certified blanks.

The Certified blank particles are included in MESF calibration set obtained from Bangs Laboratories, Inc. The particles are 7.4 micrometer compact non-magnetic polymer particles, which may be used as non-fluorescent references for flowcytometry applications as described by i.e. Schwartz in U.S. Pat. No. 5,089,416.

TABLE 4

| Sample | Description | Δ MGV Filter Cube 1 | Δ MGV Filter Cube 2 | Δ MGV Filter Cube 3 |
|---|---|---|---|---|
| A | Blank | −1 | −1 | −67 |
| B | PS/DVB | 1087 | 1851 | 1269 |
| C | PS/DVB | 833 | 829 | 426 |
| D | EX 13 | 333 | 31 | −72 |
| E | EX 14 | 77 | 18 | 7 |
| F | Ex 15 | 11 | 14 | −51 |
| G | Ex 16 | 1 | 67 | −64 |
| H | Ex 17 | 53 | 35 | −45 |

EXAMPLE 19

Measurement of Autofluorescence by Flowcytometry Instrumentation and Software

The autofluorescence of superparamagnetic particles from Example 17 was measured with BD LSR II flowcytometer from BD biosciences. The excitation source was a 488 nm solid-state laser and a 633 nm helium neon laser. The excitation and filter specifications for the different fluorescence detectors are summarized in table 5. The voltage of the PMT detectors was all set to 600 V. The statistics were carried out by setting a gate in the plot of forward scatter (FSC) against side scatter (SSC), which included the single particles only. The flowcytometer was set to count 10 000 particles with an approximate rate of 100 events per second for each sample. The area-mean was determined for each sample. For area detection the signal will decrease with a decrease in size for the same kind of particle. (Because the intensity from the flow measurement is an integral of the detected intensity profile generated when the particle is passing the objective.)

TABLE 5

Filter Settings of BD LSR II flow cytometer

| Excitation Source | Beam Splitter | Emission Filter | Detector |
|---|---|---|---|
| 488 nm laser | 505 nm long pass | 530 (30) nm | 1 |
|  | 550 nm long pass | 575 (26) nm | 2 |
|  | 685 nm long pass | 695 (40) nm | 3 |
|  | 735 nm long pass | 780 (60) nm | 4 |
| 633 nm laser | blank | 660 (20) nm | 5 |
|  | 735 nm long pass | 780 (60) nm | 6 |

Sample Preparation

All samples were diluted with phosphate buffer saline (PBS pH 7.4) prior to the analysis. The particle concentration was adjusted to give an approximate count of 100 events per second by the flowcytometer.

Results

Two different types of coated magnetic polymer particles having styrene/divinylbenzene and the coated particles of example 17 were investigated. The results given in Table 6 are also compared to commercial available calibration particles, Certified blanks.

The Certified blank particles are included in MESF calibration set obtained from Bangs Laboratories, Inc. The particles are 7.4 micrometer compact non-magnetic polymer particles, which may be used as non-fluorescent references for flowcytometry applications as described by i.e. Schwartz in U.S. Pat. No. 5,089,416.

TABLE 6

Intensity: mean channel number of singlets

| Flow Cytometry | Measured by detector | | | | | |
|---|---|---|---|---|---|---|
|  | #1 | #2 | #3 | #4 | #5 | #6 |
| Blank | 246 | 32 | 14 | 2 | 100 | 3 |
| PS/DVB | 3040 | 784 | 1088 | 416 | 212 | 50 |
| PS/DVB | 2166 | 492 | 471 | 149 | 87 | 10 |
| Ex 17 | 579 | 84 | 26 | 4 | 31 | 0 |

By use of MESF calibration kits for fluorescein isothiocyanate (FITC), phycoerythrin (PE) and PE-Cy5, received from Bangs Laboratories Inc, the measured autofluorescence can be assigned to values of Molecules of Equivalent Soluble Fluorophore (MESF). The MESF definition may be found at http://nvl.nist.gov/pub/nistpubs/jres/107/1/j71schw.pdf In Table 7 the estimated MESF values when comparing the autofluorescence to the respective calibration curves are given.

TABLE 7

| | Excitation Source 488 nm Laser Emission filter | | |
|---|---|---|---|
| | 530 (30) MESF FITC | 575 (26) MESF PE | 695 (40) MESF PE-Cy5 |
| Ex 17 | 1342 | 362 | 66 |
| PS/DVB | 7225 | 3625 | 2635 |
| PS/DVB | 5122 | 2242 | 1151 |
| Blank | 563 | 134 | 36 |

EXAMPLE 20

Incorporation of Bodipy 630/650 Giving Superparamagnetic Particles with Three Levels of Fluorescence Intensity A 10% (w/w) dispersion in dimethyl formamide of 8 μm particles, obtained by the method described in example 17, was transferred to three vials A, B and C. 5.6 mg Bodipy 630/650 succinimidyl ester (from Molecular Probes Inc.) was mixed with 11.9 mL dimethylformamide and added to the particle dispersions in the vials. In vial A, 50 g particle dispersion was mixed with 10.6 mL colour solution, in vial B 30 g particle dispersion was mixed with 0.6 mL colour solution and in vial C 30 g particles dispersion was mixed with 0.06 mL colour solution. The mixtures were shaken for 24 hours at ambient temperature and then placed on a magnet. The particles were purified with methanol, 5% triethylamine in methanol and water and diluted in phosphate buffer saline (PBS, pH 7.4). The particles were analyzed by fluorescence microscopy and flowcytometry.

Measurement by Fluorescence Microscopy

The microscopy measurements were performed with a BX-61 fluorescence microscope from Olympus, equipped with a 75 W Xenon lamp and filter cubes from Chroma Technology. The fluorescence was measured through a filter cube with excitation bandpass filter at 630(30) nm, beamsplitter at 650 nm, and emission longpass filter at 665 nm. The objective used was Uplan-Apo 20×. The camera exposure time settings were adjusted to the corresponding amount of dye attached to the particles.

All the particles were diluted with phosphate buffer saline (pH 7.4) and transferred to a capillary channel of the microscope slide, as described in example 12.

The resulting fluorescence intensities given as AMGV were calculated as in example 12. The resulting coefficient of variation (% CV) is defined as the standard deviation of mean grey value (MGV) of particles divided by the mean grey value (MGV) of particles multiplied by a factor of 100. The coloured particles were compared with similar particles without dye incorporated (blank references).

TABLE 8

| Microscopy | Exposure time (ms) | MGV Particle | MGV Background | ΔMGV | CV % |
|---|---|---|---|---|---|
| Ex 20, A | 50 | 2349 | 76 | 2273 | 10 |
| Ex 20, B | 50 | 425 | 64 | 361 | 10 |
| Ex 20, C | 100 | 153 | 64 | 89 | 8 |
| Blank | 1000 | 85 | 96 | −11 | — |

Measurements by Flowcytometry

The flowcytometry measurements were performed with a BD LSR II flowcytometer from Becton-Dickinson. The instrument was equipped with a 633 nm laser as excitation source. For detection an emission bandpass filter with specification 660(20) nm, corresponding to the APC (Allophycoerithrin) filter-settings for the BD LSR II flowcytometer, was used. The voltage of the PMT detector was set to 250 V. The statistics were carried out by setting a gate in the plot of forward scatter (FSC) against side scatter (SSC), including single particles only. The flowcytometer was set to count 10 000 particles with an approximate rate of 100 events per second for each sample. The single particle population contained typically 90% of the total number of events. The area mean and coefficient of variation was determined for each sample. The coefficient of variation (% CV) is defined as the standard deviation of singlets divided by the mean intensity of singlets, at that specific voltage, multiplied by a factor of 100.

The coloured particles were compared with similar particles without dye incorporated, named blank references. All samples were diluted with phosphate buffer saline (PBS pH 7,4) prior to the analysis. The particle concentration was adjusted to give an approximate count of 100 events per second by the flowcytometer. The results are given in Table 9.

TABLE 9

| Flow Cytometry | Intensity: Mean channel no. singlets PMT Voltage = 250 v | Intensity Distribution CV % |
|---|---|---|
| Ex 20, A | 8848 | 16 |
| Ex 20, B | 1536 | 16 |
| Ex 20, C | 153 | 42 |
| Blank | 0 | — |

EXAMPLE 21

Incorporation of Bodipy 650/665 Giving Superparamagnetic Particles with Three Levels of Fluorescence Intensity 5 μm particles obtained with the method described in example 17 were transferred into dimethylformamide giving 10% w/w dispersion. 1.5 mL of the dispersion was transferred to three vials each, A, B and C. 1.1 mg Bodipy 650/665 succinimidyl ester (from Molecular Probes Inc.) was mixed with 1.25 mL dimethylformamide. The Bodipy solution was mixed with the particles dispersions giving the following amount of dye per mg dry substance (DS) of particles; in A) 1.0 mg/g DS, in B) 0.1 mg/g DS and in C) 0.01 mg/g DS. The dispersions were shaken at ambient temperature over night. The particles were purified with a solution of 5% triethylamine in methanol and phosphate buffer saline (PBS, pH 7.4).

The particles were analyzed by fluorescence microscopy and flowcytometry as described in Example 20. The results given in Table 10 and Table 11 demonstrate that particle populations can be coloured with a large difference in intensity also for this type of dye.

TABLE 10

| Microscopy | Exposure time (ms) | MGV Particle | MGV Background | ΔMGV | CV % |
|---|---|---|---|---|---|
| Ex 21, A | 10 | 511 | 64 | 447 | 8 |
| Ex 21, B | 100 | 758 | 76 | 682 | 10 |
| Ex 21, C | 1000 | 826 | 96 | 730 | 9 |
| Blank | 50000 | 1113 | 1148 | −35 | — |

TABLE 11

| Flow Cytometry | Intensity: Mean channel no. singlets PMT Voltage = 250 v | Intensity Distribution CV % |
|---|---|---|
| Ex 21, A | 1133 | 15 |
| Ex 21, B | 192 | 15 |
| Ex 21, C | 20 | 73 |
| Blank | 0 | — |

EXAMPLE 22

Incorporation of DY-647 Giving Superparamagnetic Particles with Three Levels of Fluorescence Intensity 5 μm particles obtained with the method described in example 17 was transferred into dimethylformamide giving 10% w/w dispersion. 1.5 mL of the dispersion was transferred to three vials each, A, B and C. 1.1 mg DY-647 succinimidyl ester (from Dyomics GmbH) was mixed with 1.25 mL dimethylformamide. The dye solution was mixed with the particles dispersions giving the following amount of dye per mg dry substance (DS) of particles; in A) 1.0 mg/g DS, in B) 0.1 mg/g DS and in C) 0.01 mg/g DS. The dispersions were shaken at ambient temperature over night. The particles were purified with a solution of 5% triethylamine in methanol, water and diluted in phosphate buffer saline (PBS, pH 7.4).

The particles were analyzed by fluorescence microscopy and flowcytometry as described in Example 20. The results, given in Table 12 and Table 13, demonstrate that particle populations can be coloured with a large differences in intensity also for this type of dye (DY-647).

TABLE 12

| Microscopy | Exposure time (ms) | MGV Particle | MGV Background | ΔMGV | CV % |
|---|---|---|---|---|---|
| Ex 22, A | 10 | 1135 | 65 | 1070 | 15 |
| Ex 22, B | 100 | 1180 | 81 | 1099 | 8 |
| Ex 22, C | 1000 | 1298 | 98 | 1200 | 10 |
| Blank | 50000 | 1113 | 1148 | −35 | — |

TABLE 13

| Flow Cytometry | Intensity: Mean channel no. singlets PMT Voltage = 250 v | Intensity Distribution CV % |
|---|---|---|
| Ex 22, A | 2955 | 14 |
| Ex 22, B | 356 | 9 |
| Ex 22, C | 38 | 227 |
| Blank | 0 | — |

EXAMPLE 23

Fluorescent Particles with Narrow Intensity Distribution

5 μm particles obtained by the method described in example 17 were transferred to dimethylformamide. 15 gram of 10% (w/w) particle dispersion was mixed with 1.2 mg of DY-647 succinimidylester dissolved in 2 mL dimethylformamide. After 2 hours a small sample of the coloured particles was purified with methanol and phosphate buffer saline (PBS, pH 7.4). The sample were analysed on the flowcytometer as described in examples 20, 21 and 22 with one exception, use of slower sheath fluid flow (low setting). The result, given in Table 14, shows that the superparamagnetic beads can be coloured to give particle populations with very narrow intensity distribution.

TABLE 14

| Flow Cytometry | Intensity: Mean channel no. singlets PMT Voltage = 250 v | Intensity Distribution CV % |
|---|---|---|
| A | 2336 | 6 |

EXAMPLE 24

Colouring Prior to Coating
Colouring Procedure

Particles obtained by the method described in Example 11 were transferred to anhydrous dimethylformamide. In four different bottles, 38 gram of 5% particle dispersion was mixed with 4 mL of dimethyl formamide containing 2 mg dye. The four fluorescent dyes used, AMCA-X, Bodipy TMR, Bodipy FL (from Molecular Probes Inc) and DY?555 (from Dyomics GmbH) had succinimidyl ester functionality. After stirring for 20 hours at ambient temperature, the particles were purified several times with 5% triethylamine in methanol and finally with methanol. Prior to microscopy analyses, small samples of particles were diluted in phosphate buffer saline (pH 7.4).

Table 15 shows the fluorescence intensities of dyed particles as the DMGV value, analyzed in appropriate filter for the specific fluorophore attached to the particles.
Coating Procedure 0.3 gram of the coloured particles above, were transferred to diethylene glycol dimethyl ether. The content of particles in the dispersions were justified to 10% dry substance (DS). 2.1 gram 1,4-Butandiol diglycidylether and 2.2 gram glycidol were added to the particle suspensions. The mixtures were shaken on vortex and placed in a shaker (LabMate) at 75° C. for 20 hours. The particles were purified twice with methanol and with phosphate buffer saline (pH 7.4). Prior to microscopy analyses small samples of particles were diluted with phosphate buffer saline (pH 7.4).

Table 15 shows the fluorescence intensities of dyed and coated particles as the DMGV value, analyzed in appropriate filter for the specific fluorophore attached to the particles. The results indicate that the coumarin-dye, AMCA-X (from Molecular Probes Inc) may be a better alternative than a series of other dyes when the coating step is done after the colouring.

TABLE 15

| Dye | ΔMGV (Dyed particle) | ΔMGV (Dyed and coated particle) | Excitation filter nm | Emission filter nm | Exposure time |
|---|---|---|---|---|---|
| AMCA-X | 470 | 614 | 360 (40) | 420 LP | 10 |
| Bodipy TMR | 1137 | 66 | 550 (30) | 620 (60) | 10 |
| Bodipy FL | 1710 | 174 | 450 (50) | 520 LP | 10 |
| DY-555 | 2492 | 40 | 550 (30) | 620 (60) | 20 |

By microscopy, particles coloured with AMCA-X and coated were compared to equivalent particles without dye, blank references, detected through different filters. As can be seen in Table 16, the AMCA-dye does not disturb the detection in filters suitable for a reporter signals

TABLE 16

| Excitation filter (nm) | 360 (40) | 450 (50) | 550 (30) | 630 (30) |
|---|---|---|---|---|
| Emission filter (nm) | 420 LP | 520 LP | 620 (60) | 665 LP |
| Exposure time | 10 ms | 500 ms | 5000 ms | 50000 ms |
| Particle type | ΔMGV | ΔMGV | ΔMGV | ΔMGV |
| Blank reference | 0 | 90 | 51 | −186 |
| Dyed with AMCA and coated | 584 | 108 | 17 | −110 |

The invention claimed is:

1. A non-autofluorescent coated magnetic particle comprising:
    a porous magnetic polymer particle of a matrix polymer, said porous magnetic polymer particle having superparamagnetic crystals on a surface and within the pores thereof, wherein majority of the superparamagnetic crystals are within the pores in the porous magnetic polymer particle and wherein the porous magnetic polymer particle is essentially free of conjugated delocalised electron systems other than those found in benzene rings; and
    a coat formed of a coating polymer wherein the coating polymer is formed by the polymerization of coating monomers comprising at least one epoxide and wherein the coating monomers are essentially free of conjugated delocalised electron systems other than those found in benzene rings,
    wherein said coated magnetic particle has a coefficient of variation (CV) of less than 10%, wherein said coated magnetic particle is essentially non-autofluorescent, wherein the coated magnetic particle is essentially free of conjugated delocalised electron systems other than those found in benzene rings and having a level of autofluorescence corresponding to a difference in the Mean Grey Value (ΔMGV) at an excitation wavelength of 450±25 nm for an exposure time of 500 ms or 600 ms of less than 600.

2. The non-autofluorescent coated magnetic particle of claim 1 having a level of autofluorescence corresponding to a difference in the Mean Grey Value (ΔMGV) at an excitation wavelength of 450±25 nm for an exposure time of 500 ms or 600 ms of less than 300.

3. The non-autofluorescent coated magnetic particle of claim 1 wherein said coating polymer is formed from at least two epoxides.

4. The non-autofluorescent coated magnetic particle of claim 3 wherein the epoxides are selected from epichlorohydrin, epibromohydrin, isopropylglycidyl ether, butyl glycidyl ether, allylglycidyl ether, 1,4-butanediol diglycidyl ether (1,4-bis (2,3-epoxypropoxy)butane), ethylhexylglycidylether, methyl glycidylether, neopentylglycol diglycidyl ether, ethylene glycol diglycidyl ether, glycerol diglycidyl ether, glycidol, and glycidyl methacrylate.

5. The non-autofluorescent coated magnetic particle of claim 1 wherein the polymer particle has a diameter in the range 0.8 to 10 µm.

6. The non-autofluorescent coated magnetic particle of claim 5 wherein the particle is in the range 2 to 10 µm in diameter.

7. The non-autofluorescent coated magnetic particle of claim 1 wherein said matrix polymer is a combination of a styrenic polymer, a styrenic/acrylic polymer and an acrylic polymer.

8. The non-autofluorescent coated magnetic particle of claim 1 wherein the particle surface carries free amino groups.

9. The non-autofluorescent coated magnetic particle of claim 1 additionally comprising a fluorophore or mixture of different fluorophores.

10. The non-autofluorescent coated magnetic particle of claim 9 wherein said fluorophore is attached to the external coating polymer via an amino linkage or is swollen into the coating polymer and entrapped therein.

11. The non-autofluorescent coated magnetic particle of claim 9 wherein said fluorophore is Bodipy 630/650, Bodipy 650/655, DY-647 or AMCA-X.

12. The non-autofluorescent coated magnetic particle of claim 9 wherein said fluorophore emits in the blue/green region of the electromagnetic spectrum.

13. The non-autofluorescent coated magnetic particle of claim 1 or claim 9 additionally comprising an affinity ligand.

14. A mixture of coated magnetic particles as claimed in claim 1 wherein the CV of the polymer particle diameters is less than 8%.

15. The mixture of coated magnetic particles as claimed in claim 14 comprising at least a first set of coated magnetic particles carrying a first fluorophore and second set of coated magnetic particles carrying a second fluorophore, the particles, of said first and second sets being of differing diameters.

16. A process for the preparation of essentially non-autofluorescent coated porous magnetic particles, comprising the steps of:
(a) providing a solution comprising porous magnetic polymer particles, said porous magnetic polymer particle are essentially free of conjugated delocalised electron systems other than those found in benzene rings and essentially free from surface nitro groups and having superparamagnetic crystals on the surface and within the pores thereof, wherein majority of the superparamagnetic crystals are within pores in the porous magnetic polymer particle;
(b) providing a solution comprising coating monomers selected from epoxides which are essentially free of conjugated delocalised electron systems other than those found in benzene rings;
(c) combining the solution comprising the porous magnetic polymer particles with the solution comprising the coating monomers under conditions to form coating polymers from the coating monomers that coat the porous magnetic polymer particles, and
(d) isolating the coated porous magnetic particles which are essentially free of conjugated delocalised electron systems other than those found in benzene rings, which have a coefficient of variation (CV) of less than 10% and wherein the coated magnetic particle is essentially non-autofluorescent and having a level of autofluorescence corresponding to a difference in the Mean Grey Value (ΔMGV) at an excitation wavelength of 450±25 nm for an exposure time of 500 ms or 600 ms of less than 600.

17. The non-autofluorescent coated magnetic particle of claim 1, wherein the porous magnetic polymer particle comprising the superparamagnetic crystals is further surface functionalized with a molecule selected from the group consisting of a sulphonic acid, a carboxylic acid, an amine, or an epoxy group.

18. The non-autofluorescent coated magnetic particle of claim 1, wherein the porous magnetic polymer particle comprising the superparamagnetic crystals is essentially free from any surface nitro groups.

19. The non-autofluorescent coated magnetic particle of claim 7, wherein the matrix polymer is comprised of monomers selected from the group consisting of methyl methacrylate, methacrylic acid, hydroxyethyl methacrylate, glycidyl methacrylate, butylmethacrylate, acrylic acid, ethyleneglycol, dimethacrylate, trimethylolpropane trimethacrylate, trimethylol triacrylate, pentaerythritol tetraacrylate and other acrylic or methacrylic monomers.

* * * * *

UNITED STATES PATENT AND TRADEMARK OFFICE
CERTIFICATE OF CORRECTION

PATENT NO. : 8,722,429 B2  
APPLICATION NO. : 12/486590  
DATED : May 13, 2014  
INVENTOR(S) : Weng et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this  
Twenty-eighth Day of July, 2015

Michelle K. Lee  
*Director of the United States Patent and Trademark Office*